United States Patent
Hickle

(10) Patent No.: US 7,578,802 B2
(45) Date of Patent: Aug. 25, 2009

(54) USER AUTHORIZATION SYSTEM AND METHOD FOR A SEDATION AND ANALGESIA SYSTEM

(75) Inventor: Randall S. Hickle, Lubbock, TX (US)

(73) Assignee: Scott Laboratories, Inc., Lubbock, TX (US)

(*) Notice: Subject to any disclaimer, the term of this patent is extended or adjusted under 35 U.S.C. 154(b) by 585 days.

(21) Appl. No.: 10/439,323

(22) Filed: May 16, 2003

(65) Prior Publication Data

US 2004/0039257 A1    Feb. 26, 2004

Related U.S. Application Data

(60) Provisional application No. 60/378,058, filed on May 16, 2002.

(51) Int. Cl.
*A61M 37/00* (2006.01)
(52) U.S. Cl. .................................... 604/131; 604/65
(58) Field of Classification Search ................. 600/300, 600/544; 604/131, 67, 890.1, 891.1, 65–66; 463/29
See application file for complete search history.

(56) References Cited

U.S. PATENT DOCUMENTS

| | | | |
|---|---|---|---|
| 5,041,086 A * | 8/1991 | Koenig et al. ................. 604/65 |
| 5,401,059 A | 3/1995 | Ferrario |
| 5,845,255 A * | 12/1998 | Mayaud ........................ 705/3 |
| 6,132,363 A * | 10/2000 | Freed et al. .................. 600/16 |
| 6,188,570 B1 | 2/2001 | Borkowski |
| 6,292,899 B1 | 9/2001 | McBride ..................... 713/200 |
| 6,519,569 B1 * | 2/2003 | White et al. ................... 705/3 |
| 6,611,733 B1 | 8/2003 | De La Huerga |
| 2001/0041920 A1 * | 11/2001 | Starkweather et al. ........ 607/60 |
| 2002/0017296 A1 | 2/2002 | Hickle |
| 2002/0017299 A1 | 2/2002 | Hickle |
| 2002/0017300 A1 | 2/2002 | Hickle et al. |
| 2002/0038392 A1 * | 3/2002 | De La Huerga ................ 710/8 |

FOREIGN PATENT DOCUMENTS

| | | |
|---|---|---|
| EP | 0 869 460 A2 | 7/1998 |
| EP | 0 869 460 A3 | 3/1999 |
| WO | 99/13415 | 3/1999 |
| WO | WO/99/62403 | 12/1999 |
| WO | WO/01/95971 | 12/2001 |

OTHER PUBLICATIONS

International Search Report dated Dec. 10, 2003 for PCT/US03/15430.

* cited by examiner

*Primary Examiner*—Nicholas D Lucchesi
*Assistant Examiner*—Christopher D Koharski
(74) *Attorney, Agent, or Firm*—Hogan & Hartson LLP

(57) ABSTRACT

The present invention comprises a security system integral with a sedation and analgesia system. The invention includes a computer assisted IV drug infusion administration device coupled with a secure user interface, or other security means, that can restrict and monitor user access to prevent unauthorized or improper use of the device. The system can also provide varying levels of access to the device so that different users may have different levels of access to system operations. The variety of access levels may prevent accidental or intentional misuse of the drug delivery system, while still permitting access to the required functionality. Data, such as usage statistics and procedural events associated with drug delivery, may be recorded in association with a user's personal identification information to help identify training needs and to identify possible misuse of access information.

20 Claims, 3 Drawing Sheets

USER AUTHORIZATION SYSTEM AND METHOD FOR A SEDATION AND ANALGESIA SYSTEM

CROSS REFERENCE TO RELATED APPLICATIONS

This application claims priority under 35 U.S.C. §119(e) to U.S. Provisional Patent Application No. 60/378,058, "User Authorization System and Method for a Sedation and Analgesia System," filed May 16, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates, in general, to security systems and, more particularly, to security systems associated with the operation of medical devices.

2. Description of the Related Art

A sedation and analgesia system was developed to provide patients undergoing painful, uncomfortable or otherwise frightening (anxiety inspiring) medical or surgical procedures with a means for receiving sedative, analgesic, and/or amnestic drugs safely in a way that reduces the risk of overmedication with or without the presence of a licensed anesthesia provider. By reducing the number of potential failure modes potentially associated with anesthesia machines, a sedation and analgesia systems has been rendered safer for use in hospital and ambulatory environments and may be operated by individuals other than trained anesthesiologists such as, for example, certified registered nurse anesthetists, trained physicians, or other licensed operators. The sedation and analgesia system has gone far to meet the anesthesia needs of office based practitioners who are unable to afford or schedule anesthesia providers for every procedure where sedation and analgesia would be beneficial. The advent of a sedation and analgesia system devoted to these purposes provides these individuals with a drug delivery system integrated into a patient monitoring system that decreases the manual tasks and cognitive load that may be required by anesthesia machines, yet gives the clinician ultimate decision making responsibility following a "clinician knows best" philosophy. The reduction of many manual activities associated with anesthesia machines allows for a sedation and analgesia system to be operated without an anesthesia provider in ambulatory settings providing the patient with a cost-effective and readily available means of sedation.

However, the relatively easy operation of the sedation and analgesia system may lead to its inappropriate use by clinicians who have not been properly trained. Though the sedation and analgesia system has been designed for efficient and easy use by non-anesthetist practitioners, such systems remain sufficiently complex to require appropriate training before being used on patients. Because the sedation and analgesia system is designed to be an efficient, easily operable system, untrained clinicians may be tempted to use such systems on patients without having received formal training. If sedation and analgesia systems are used in such a manner by uncertified persons, patients may be put at considerable risk.

The potential for abuse of sedation and analgesia systems is also present in recreational drug users with access to such systems. Designed to prevent an overdose of medication to a patient during authorized medical procedures, recreational drug users may feel that they can use sedation and analgesia systems to self-administer narcotics and/or other illicit drugs safely. Use of the system for such purposes may result in severe adverse consequences due to the addiction to illicit drugs or overdose resulting from the use of drugs whose effects and concentrations may not be accounted for by the pharmacokinetic model of the sedation and analgesia system. The need has therefore arisen for a sedation and analgesia system that permits only authorized and properly trained clinicians to operate the system.

Chronic misuse of sedation and analgesia systems, even by trained individuals, may also result in severe patient complications. Such users may have access to sedation and analgesia systems, yet have insufficient training or experience to ensure patient safety during procedures involving sedation and analgesia. The need has therefore arisen for a sedation and analgesia system that records the personal information of a user as well as the presence or absence of critical system or patient episodes in order to ascertain whether users may require additional training in order to be allowed access to sedation and analgesia systems.

BRIEF SUMMARY OF THE INVENTION

The present invention solves the aforementioned drawbacks of automated drug infusion devices by providing security devices and methods for sedation and analgesia systems. The invention includes a computer assisted IV drug infusion administration device coupled with a secure user interface, or other security means, that can restrict and monitor user access to prevent unauthorized or improper use of the device.

It is an object of the present invention to provide a computer assisted IV drug infusion administration device that permits only authorized and properly trained clinicians to operate the system. Providing varying levels of access to the device so that different users may have different levels of access to system operations can further control access.

It is a further object of the present invention to provide a sedation and analgesia system that records the personal information of a user as well as the presence or absence of critical system or patient episodes or critical incidents in order to ascertain whether users may require additional training in order to be allowed, or to retain, access to sedation and analgesia systems.

In one embodiment, the present invention uses a security prompt incorporated into the user interface of the delivery device that requires a user to provide a personal identification number (PIN), fingerprint, voice command, data card, or other identification means such as biometric data prior to operating the system. Data relating to authorized identification entries is stored in a memory device included in the delivery device. In the case where unrecognized personal access information is provided to the system, the system's drug delivery functionality may remain disabled.

The present invention may also incorporate a plurality of security levels associated with different types of users. For example, one level of access can be granted to the extent required for maintenance only, while a greater level of access can be granted for clinician use. Access for administrative purposes is also feasible. The variety of access levels may prevent accidental or intentional misuse of the drug delivery system, while tailoring access to the required functionality.

Data, such as usage statistics and procedural events associated with drug delivery, may be recorded in association with a user's personal identification information. Such recorded data may be used to help identify training needs, for quality assurance purposes and to identify possible misuse of access information.

DETAILED DESCRIPTION OF THE INVENTION

Figure 1:
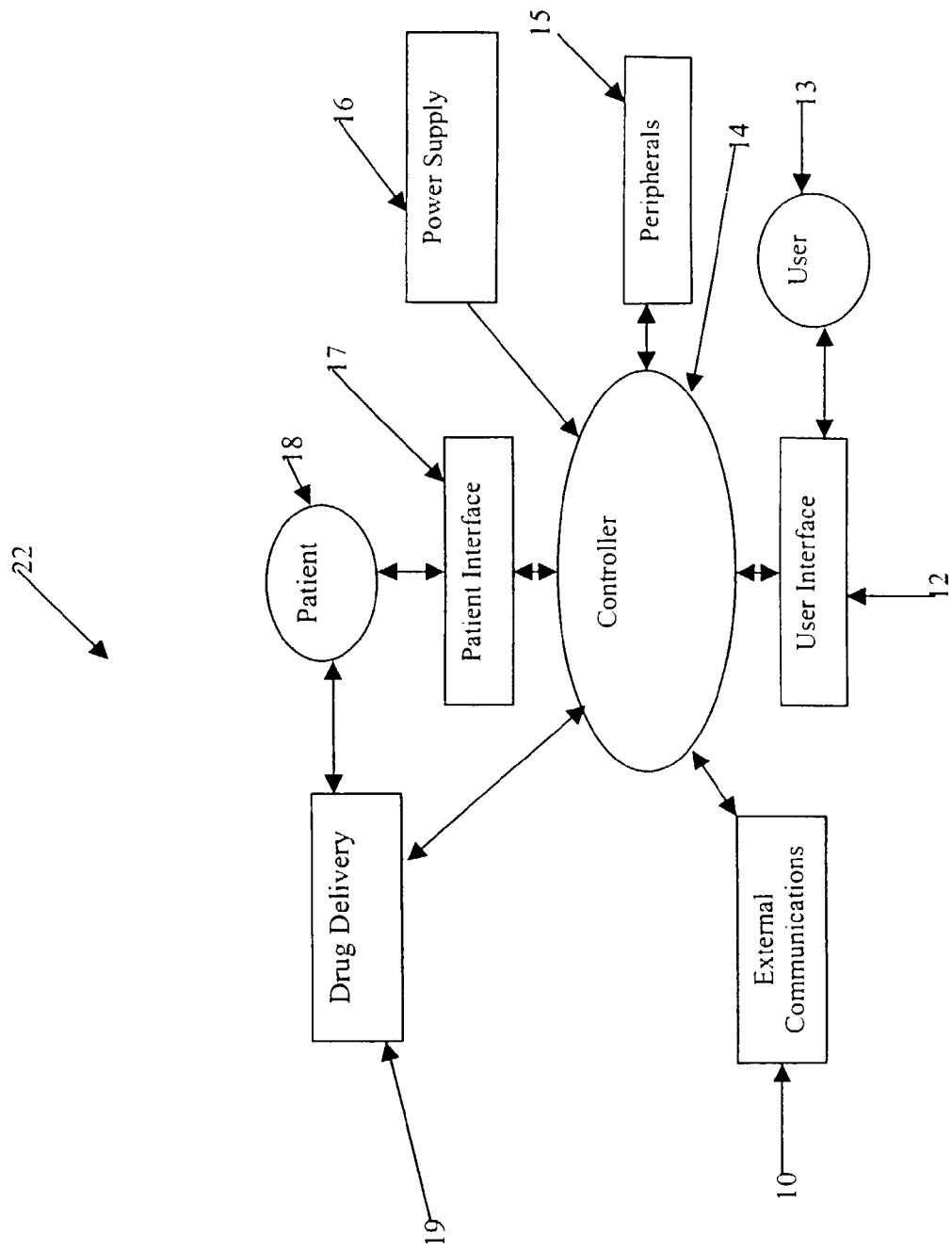
FIG. 1 illustrates an overview block diagram of one embodiment of a sedation and analgesia system in accordance with the present invention.

FIG. 1 illustrates a block diagram depicting one embodiment of the present invention comprising sedation and analgesia system 22 having user interface 12, software controlled controller 14, peripherals 15, power supply 16, external communications 10, patient interface 17, and drug delivery 19, where sedation and analgesia system 22 is operated by user 13 in order to provide sedation and/or analgesia to patient 18. A sedation and analgesia system 22 is disclosed and enabled in commonly assigned and co-pending U.S. patent application Ser. No. 09/324,759, filed Jun. 3, 1999 and incorporated herein by reference in its entirety. Embodiments of user interface 12 are disclosed and enabled in commonly assigned and co-pending U.S. patent application Ser. No. 10/285,689, filed Nov. 1, 2002 and incorporated herein by reference in its entirety.

The sedation and analgesia system of application Ser. No. 09/324,759 includes a patient health monitor device adapted so as to be coupled to a patient and generate a signal reflecting at least one physiological condition of the patient, a drug delivery controller supplying one or more drugs to the patient, a memory device storing a safety data set reflecting safe and undesirable parameters of at least one monitored patient physiological condition, and an electronic controller interconnected between the patient health monitor, the drug delivery controller, and the memory device storing the safety data set; wherein said electronic controller receives said signals and in response manages the application of the drugs in accord with the safety data set.

Figure 2:
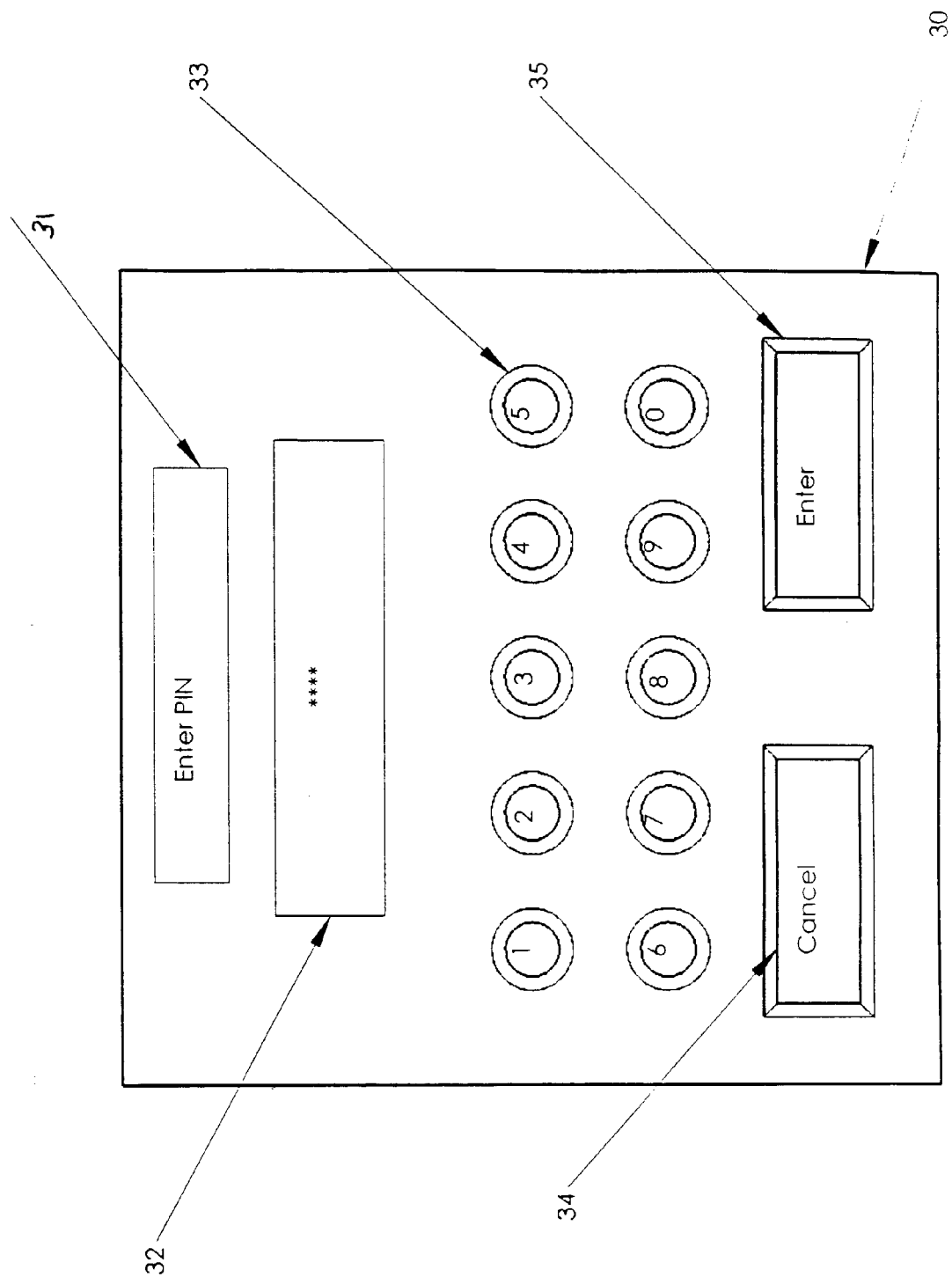
FIG. 2 illustrates one embodiment of a security prompt in accordance with the present invention.

FIG. 2 illustrates one embodiment of security prompt 30, where security prompt 30 may be incorporated into user interface 12. User interface 12 may be any suitable means for allowing user 13 to interface with sedation and analgesia system 22 such as, for example, a touch-sensitive screen, soft buttons, hard buttons, and/or a partially or completely voice activated system. Security prompt 30 may comprise text box 31, where text box 31 comprises any textual and/or iconic information capable of indicating to user 13 that he must input suitable authorized identification information in order to be allowed access to sedation and analgesia system 22. For example, if a personal identification number (PIN) security system is implemented into sedation and analgesia system 22, text box 31 may read "Enter PIN." Security prompt 30 further may comprise data display 32, where data display 32 may be any textual and/or iconic information indicative of the authorized identification information entered by user 13. For example, in the case of a PIN security system, data display 32 may indicate an asterisk (*) for every numeral entered by user 13 in order to indicate to user 13 that a character has been entered, while at the same time maintaining the privacy of the identification information of user 13 towards other individuals in sight of prompt 30. Data display 32 may further comprise a textual display, such as the phrase "data entered," or any other suitable text and/or icon such as, for example, a display of actual data entered, a symbolic representation of data entered, and/or displays relating to completed data entry if data has been entered into security prompt 30. Data display 32 may further comprise an audio component, where audio signals may be initiated at the press of input buttons 33, successful entry of authorized user information, or for any other suitable reason. Buttons 33 may also provide tactile feedback to a user when pressed so that the user knows a button has been pressed.

Input buttons 33 of security prompt 30 may be touch buttons, soft buttons, hard buttons, or any other suitable means of inputting secure data. In one embodiment of the present invention, security prompt 30 comprises a plurality of input buttons 33, having integers from 0-9 listed sequentially on 10 input buttons 33, where user 13 is required to input a personal identification number that is any suitable combination of any number of input buttons 33. Input buttons 33 may further comprise text, case specific text, icons, and/or and suitable combination of numerals. Security prompt 30 further comprises enter button 35, where enter button 35 may be depressed or otherwise initiated by user 13 to confirm a PIN entry. Security prompt 30 further comprises cancel button 34, where cancel button 34 may be depressed or otherwise initiated by user 13 if user 13 makes an error in inputting his/her PIN number. Requiring user 13 to input authorized user identification such as, for example, a personal identification number, diminishes the possibility that untrained clinicians, recreational drug users, or other unauthorized individuals will be able to gain access and misuse the system. Other embodiments of the system of the present invention may include alphanumeric buttons 33 so that the security information entered by user 13 can be more complex than a PIN or more easily remembered by the user.

The present invention further may provide an error prompt (not shown) in the event that an invalid PIN is entered into security prompt 30, where user 13 may be required to reenter their PIN or other suitable personal identification information. Authorized PIN entries for each user may be pre-programmed into the system, with each user having the ability to change the user's PIN once access to the system has been granted. Data relating to authorized PIN entries may be stored in controller 14 in a hard drive, flash disk, super disk, or other suitable data storage device. Authorized PIN entries may be transmitted to sedation and analgesia system 22 via wireless communications such as, for example, by incorporated wireless Ethernet into sedation and analgesia system 22. Authorized PIN entries may also be transmitted to sedation and analgesia system 22 over hardwired lines such as, for example, RS-232 or Ethernet connections.

In one embodiment of the present invention, sedation and analgesia system 22 comprises a plurality of security levels, where individuals may be authorized for maintenance access, clinician access, administration access, or other suitable levels of access to sedation and analgesia system 22. For example, a PIN entry corresponding to maintenance access may allow user 13 access to basic system features in order to ensure sedation and analgesia system 22 functionality, yet disallow the insertion of a drug vial into drug delivery 19 or other function. Providing only limited access to maintenance personnel or other groups further diminishes the probability of misuse of the system by unauthorized individuals. Clinicians may, for example, be allowed access to drug delivery capabilities of sedation and analgesia system 22, yet may not be given access to functionalities such as PIN authorization or other administrative features. Denying clinicians access to, and the ability to enter and/or change authorization codes, may prevent the accidental or intentional misuse of sedation and analgesia system 22. Administrators may be given access to authorization codes, yet may not be given access to the features of sedation and analgesia system 22 related to drug delivery and/or patient 18 care.

The present invention further comprises storing general data relating to the use of sedation and analgesia system 22, where the data may be stored in connection with the personal identification number of user 13. Data may be stored in a flash disk, super disk, hard drive, transmitted to a server for storage, or stored in any other suitable manner. Data stored may be related to duration of use by user 13, number of times user 13 has accessed sedation and analgesia system 22, at what time during the day user 13 accessed sedation and analgesia system 22, information related to administration of drugs, information related to negative procedural events, or any other suitable data for ascertaining whether misuse of sedation and analgesia system 22 has occurred. Recording data related to sedation and analgesia system 22 use may also help identify a user who may need additional training if a number of system failures or critical incidents are attributable to that user.

The present invention may further comprise incorporating any suitable security device into sedation and analgesia system 22 such as, for example, a retinal scanner, fingerprint scanner, biometric scanner, voice recognition system, or a magnetic strip identification card system for the verification of the authority of a user to perform a functionality of the system 22. Any suitable combination of a plurality of security devices is further consistent with the present invention.

Figure 3:
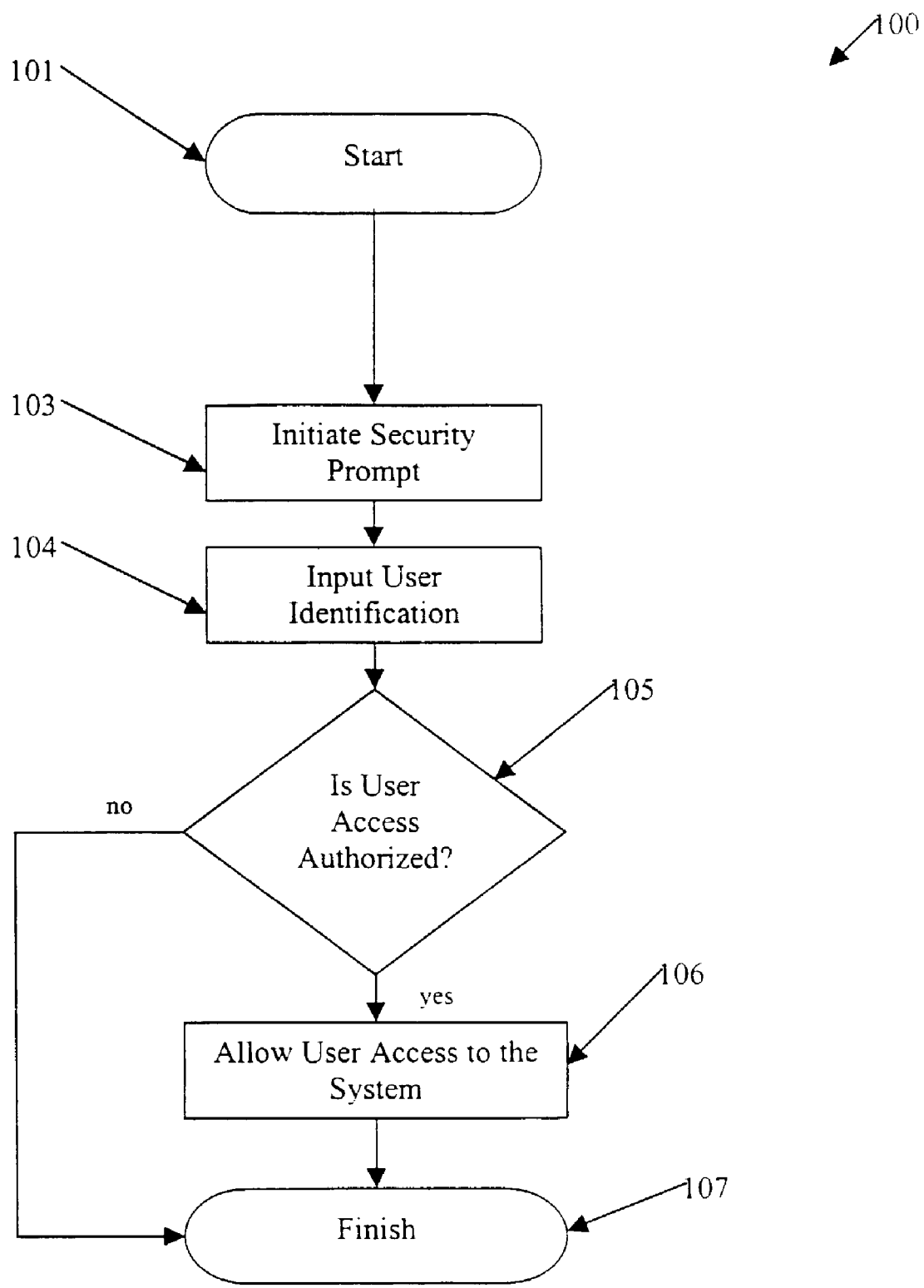
FIG. 3 illustrates one embodiment of a method of using a security system integrated with a sedation and analgesia system in accordance with the present invention.

FIG. 3 illustrates one embodiment of method 100 in accordance with the present invention, where method 100 comprises start step 101. In one embodiment of the present invention, start step 101 comprises providing a sedation and analgesia system integrated with a user authorization security system and delivering power to the integrated sedation and analgesia system 22. The user authorization security system may be a PIN authorization system, retinal scanner, fingerprint scanner, magnetic strip identification card system, and/or any other suitable user authorization system. Following start step 101, method 100 may proceed to step 103.

In one embodiment of the present invention, step 103 comprises initiating security prompt 30, where security prompt 30 may be displayed on user interface 12. Further embodiments of security prompt 30 may request user 13 to participate in a retinal scan, fingerprint scan, enter their PIN, and/or request user 13 to scan their identification card in an identification card scanner. Security prompt 30 may further indicate whether user 13 has gained access and what level of access to sedation and analgesia system 22 they have received. Following step 103, method 100 may proceed to step 104.

In one embodiment of the present invention, step 104 comprises user 13 inputting their user identification into sedation and analgesia system 22. User 13 input comprises user 13 subjecting themselves to a retinal scan, fingerprint scan, entering their PIN, swiping their identification card, and/or any other suitable means of inputting personal identification for authorization. Once user 13 has input their personal identification information, method 100 may proceed to query 105.

Query 105 comprises controller 14 determining whether the personal identification information input by user 13 matches the personal information of those individuals who are allowed access to sedation and analgesia system 22. Controller 14 may further determine what level of access user 13 is granted such as, for example, maintenance access, clinician access, or administrative access. Authorized personal identification information may be stored in controller 14 in the form of a flash disk, super disk, hard drive, or other suitable storage means. In one embodiment of the present invention, sedation and analgesia system 22 is connected to an intranet and/or extranet, where user identification may be authorized from a remote location. User 13 input may also be used for billing purposes, where user 13 may be charged per use of sedation and analgesia system 22. For example, if user 13 is an authorized clinician licensed to operate sedation and analgesia system 22, but maintenance, use, software, or other fees have not been paid, user 13 may be denied access to sedation and analgesia system 22 and/or provided an explanation as to the reason why access was denied.

If the personal identification of user 13 does not correspond to the data stored in sedation and analgesia system 22, method 100 may proceed to finish step 107. In one embodiment of the present invention, finish step 107 comprises placing or retaining sedation and analgesia system 22 in a powered state where patient monitoring and drug delivery 19 functionality are disabled. Finish step 107 may disable sedation and analgesia system 22 functionality and prevent user 13 from monitoring or delivering drugs to patient 18. Finish step 107 further comprises fully powering down sedation and analgesia system 22.

If the personal identification of user 13 corresponds to the data stored in sedation and analgesia system 22, method 100 may proceed to step 106. Step 106, in one embodiment of the present invention, comprises providing user 13 access to the features of sedation and analgesia system 22 consistent with their authorization level as indicated by their personal identification. For example, user 13 may enter a PIN, and controller 14 will determine that user 13 is authorized for maintenance access only. Sedation and analgesia system 22 will then limit the functionality of sedation and analgesia system 22 to only those features that pertain to the needs of maintenance personnel. Once user 13 has accessed sedation and analgesia system 22 and completed their work, method 100 may proceed to finish step 107.

While exemplary embodiments of the invention have been shown and described herein, it will be obvious to those skilled in the art such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope by the claims as they will be allowed.

The invention claimed is:

1. A sedation and analgesia system comprising:
   a patient health monitor device adapted so as to be coupled to a patient and generate a signal reflecting at least one physiological condition of the patient;
   a user interface allowing a user to enter inputs;
   a drug delivery controller supplying one or more drugs to the patient;
   an electronic controller operably connected to the patient health monitor, and the drug delivery controller, wherein said electronic controller receives said signal and in response manages the application of the drugs in accord with stored parameters of at least one monitored patient physiological condition; and a security system incorporated into said user interface that requires said user to input authorized personal identification information so as to restrict unauthorized use of said sedation and analgesia system, wherein information related to negative procedural events during the use of said sedation and analgesia system is recorded in association with said authorized personal identification information of said user and said information related to negative procedural events is used to determine future authorization of said user, and wherein administrative access to the sedation and analgesia system is separable from access to features of the sedation and analgesia system related to drug delivery and/or patient care.

2. The sedation and analgesia system according to claim 1, wherein said security system comprises a security prompt that requires said user to input said authorized personal identification information before said sedation and analgesia system is enabled for operation.

3. The sedation and analgesia system according to claim 2, wherein data relating to said authorized personal identification information is stored in a memory device associated with said sedation and analgesia system.

4. The sedation and analgesia system according to claim 3, wherein said authorized personal identification information is at least one of a personal identification number, a retinal scan, a fingerprint, a biometric scan, a voice recognition command, and a magnetic strip identification card.

5. The sedation and analgesia system according to claim 3, wherein said authorized personal identification information is transmitted to said sedation and analgesia system via wireless communications.

6. The sedation and analgesia system according to claim 3, wherein said security system comprises a plurality of security levels that permits access to varying functionalities of said sedation and analgesia system.

7. The sedation and analgesia system according to claim 6, wherein said plurality of security levels includes a maintenance access level, an administration access level, and a clinician access level.

8. The sedation and analgesia system according to claim 3, wherein general data relating to the use of said sedation and analgesia system is recorded in association with said authorized personal identification information of said user.

9. The sedation and analgesia system according to claim 8, wherein said general data comprises at least one of a duration of use by said user, a number of times said user has accessed said sedation and analgesia system, a time of day said user accessed said sedation and analgesia system, and information related to administration of drugs.

10. The sedation and analgesia system according to claim 8, wherein said general data comprises system failures, such that training needs can be identified for said user associated with said data.

11. A method of operating a sedation and analgesia system comprising the steps of:
connecting to a patient a drug delivery device having a drug delivery controller supplying one or more drugs, said drug delivery controller being coupled to an electronic controller which controls the delivery of the drugs to the patient;
attaching at least one patient health monitor device to a patient, which health monitor device generates a value reflecting at least one physiological condition of a patient and is coupled to said electronic controller;
inputting into a security system identification information of an authorized user to enable operation of said sedation and analgesia system;
accessing a safety data set reflecting parameters of at least one patient physiological condition;
delivering the drugs to the patient in accord with the safety data set, and
recording information related to negative procedural events during the use of said sedation and analgesia system in association with said security system identification information wherein said information related to negative procedural events is used to determine future authorization of said user, and wherein administrative access to said information is separable from access to features of the sedation and analgesia system related to drug delivery and/or patient care.

12. The method of operating a sedation and analgesia system according to claim 11, further comprising the step of pre-programming said security system to accept particular authorized identification information.

13. The method of operating a sedation and analgesia system according to claim 12, wherein data relating to said authorized identification information is stored in a memory device associated with said sedation and analgesia system.

14. The method of operating a sedation and analgesia system according to claim 13, wherein said authorized identification information is at least one of a personal identification number, a retinal scan, a fingerprint, a biometric scan, a voice recognition command, and a magnetic strip identification card.

15. The method of operating a sedation and analgesia system according to claim 13, wherein said authorized identification information is transmitted to said sedation and analgesia system via wireless communications.

16. The method of operating a sedation and analgesia system according to claim 13, wherein said security system comprises a plurality of security levels that permits access to varying functionalities of said sedation and analgesia system.

17. The method of operating a sedation and analgesia system according to claim 16, wherein said plurality of security levels includes a maintenance access level, an administration access level, and a clinician access level.

18. The method of operating a sedation and analgesia system according to claim 13, wherein general data relating to the use of said sedation and analgesia system is recorded in association with said authorized identification information of said user.

19. The method of operating a sedation and analgesia system according to claim 18, wherein said general data comprises at least one of a duration of use by said user, a number of times said user has accessed said sedation and analgesia system, a time of day said user accessed said sedation and analgesia system, and information related to administration of drugs.

20. The method of operating a sedation and analgesia system according to claim 18, wherein said general data comprises system failures, such that training needs can be identified for said user associated with said data.

* * * * *

UNITED STATES PATENT AND TRADEMARK OFFICE
CERTIFICATE OF CORRECTION

PATENT NO. : 7,578,802 B2 Page 1 of 1
APPLICATION NO. : 10/439323
DATED : August 25, 2009
INVENTOR(S) : Randall S. Hickle It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 968 days.

Signed and Sealed this

Seventh Day of September, 2010

David J. Kappos
*Director of the United States Patent and Trademark Office*